(12) United States Patent
Myllärinen

(10) Patent No.: US 9,854,821 B2
(45) Date of Patent: Jan. 2, 2018

(54) CASEIN PROTEIN PRODUCT

(71) Applicant: VALIO LTD, Helsinki (FI)

(72) Inventor: Päivi Myllärinen, Helsinki (FI)

(73) Assignee: VALIO LTD., Helsinki (FI)

( * ) Notice: Subject to any disclaimer, the term of this patent is extended or adjusted under 35 U.S.C. 154(b) by 0 days.

(21) Appl. No.: 14/409,904

(22) PCT Filed: Jun. 26, 2013

(86) PCT No.: PCT/FI2013/050705
§ 371 (c)(1),
(2) Date: Dec. 19, 2014

(87) PCT Pub. No.: WO2014/001642
PCT Pub. Date: Jan. 3, 2014

(65) Prior Publication Data
US 2015/0148283 A1    May 28, 2015

(30) Foreign Application Priority Data
Jun. 27, 2012 (FI) ...................................... 20125735

(51) Int. Cl.
*A23J 3/10* (2006.01)
*C07K 14/47* (2006.01)

(52) U.S. Cl.
CPC ............. *A23J 3/10* (2013.01); *C07K 14/4732* (2013.01); *A23V 2002/00* (2013.01)

(58) Field of Classification Search
CPC ... A23J 3/10; C07K 14/4732; A23V 2002/00; A23V 2250/54246
See application file for complete search history.

(56) References Cited

U.S. PATENT DOCUMENTS 6,093,424 A    7/2000    Han et al.

FOREIGN PATENT DOCUMENTS

| EP | 1 061 811 | 8/2001 |
|---|---|---|
| EP | 1 197 152 | 4/2002 |
| EP | 1 442 663 | 8/2004 |
| EP | 1 467 628 | 4/2006 |
| EP | 1 588 626 | 10/2008 |
| EP | 1 772 060 | 9/2009 |
| EP | 1 643 850 | 3/2010 |
| FI | 20095500 | 11/2010 |
| FI | 20115607 | 12/2012 |
| WO | WO 96/08155 | 3/1996 |
| WO | WO 2005/013710 | 2/2005 |
| WO | WO 2008/017499 | 2/2008 |
| WO | WO 2011/039414 | 4/2011 |
| WO | WO 2011/051557 | 5/2011 |

OTHER PUBLICATIONS

Milk Protein, from http://www.milkfacts.info/Milk%20Composition/Protein.htm, pp. 1-4, accessed Mar. 4, 2015.*
Nutrient Content of Milk Varieties, from http://web.archive.org/web/20111005173904/http://www.milkfacts.info/Nutrition%20Facts/Nutrient%20Content.htm, pp. 1-15, available online on Oct. 5, 2011.*
International Search Report for PCT/FI2013/050705 dated Dec. 19, 2013.
Search Report for FI 20125735, dated Mar. 27, 2013.
M.P. Bönisch et al., "Effect of Ultra-high Temperature Treatment on the Enzymatic Cross-linking of Micellar Casein and Sodium Caseinate by Transglutaminase", Journal of Food Science, vol. 69, No. 8, Oct. 31, 2004, pp. E398-E404.
R. Sharma et al., "Influence of Transglutaminase Treatment of Skim Milk on the Formation of [epsilon]-([gamma] -glutamyl) lysine and the susceptibility of individual proteins towards crosslinking", International Dairy Journal, vol. 11, No. 10, 2001, pp. 785-793.
Covacevich, H.R., et al., "Mozzerella and chedder cheese manufacture by ultrafiltration principles", J. Dairy Sci. 1978, vol. 61, pp. 701-709.
Bütikofer et al., "Occurrence of the Angiotension-Converting Enzyme-Inhibiting Tripeptides Val-Pro-Pro and Ile-Pro-Pro in Different Cheese Varieties of Swiss Origin", J. Dairy Sci. 2008, vol. 91, pp. 29-38.
Bönisch et al., "Influence of Transglutaminase Protein Cross-Linking on the Rennet Coagulation of Casein", ScienceDirect, Food Hydrocolloids, vol. 22, No. 2 (2008), pp. 288-297.
Kuraishi et al., "Transglutaminase: Its Utilization in the Food Industry", Food Reviews International, (2001), No. 17, vol. 2, pp. 221-246.
Russian Office Action issued in App. No. 2015101334/10(001931) dated Apr. 4, 2017 (with partial translation).

* cited by examiner

*Primary Examiner* — Julie Ha
*Assistant Examiner* — Li Ni Komatsu
(74) *Attorney, Agent, or Firm* — Nixon & Vanderhye P.C.

(57) ABSTRACT

The present invention relates to a process for producing a casein protein product comprising the steps of: —providing a casein concentrate starting material, —heat-treating the material, —cooling the heat-treated material, —subjecting the cooled material to a treatment with a crosslinking enzyme, —optionally subjecting the cooled material to a treatment with a coagulant and —processing the material into the casein protein product/allowing the casein protein product to form.

11 Claims, No Drawings

CASEIN PROTEIN PRODUCT

This application is the U.S. national phase of International Application No. PCT/FI2013/050705 filed 26 Jun. 2013 which designated the U.S. and claims priority to FI 20125735 filed 27 Jun. 2012, the entire contents of each of which are hereby incorporated by reference.

FIELD OF THE INVENTION

The invention relates to a method for preparing a casein protein product. Further, the invention relates to a casein protein product comprising casein, lactose, calcium, phosphorus and biologically active peptides.

BACKGROUND OF THE INVENTION

Raw milk contains in addition to water (about 87%), fat (about 4.5%), lactose (about 5%) and protein (about 3.3%) also minerals and trace elements, such as calcium, magnesium, phosphorus, manganese, potassium, sodium, iodine and zinc. Further, milk contains also vitamins, such as A, K, B12, B6 and B2. The amino acid composition of milk proteins has better biological value than any other protein (red or white meat). Milk proteins contain a lot of so-called essential amino acids like lysine, leucine and isoleucine. The proteins of milk belong to casein or whey proteins. Typically the ratio of casein protein to whey protein in cow's milk is about 80:20. The major whey proteins in milk are beta-lactoglobulin and alpha-lactalbumin having molecular sizes of 14-18 kDa. Casein make up about 80% of the proteins in cow milk and are divided into alpha-, beta- and kappa-caseins. The molecular sizes of caseins are in the range of 19-23 kDa. In milk, casein exists in groups of molecules that are called micelles. These particles/micelles consist of casein, calcium, inorganic phosphate and citrate ions. In one casein particle there are about 20 000 single casein protein molecules. Casein particle has a porous structure containing water about 3 g per 1 g of casein.

Amino acids of animal- and plant-based proteins may be cross-linked by enzymes, such as transglutaminase, laccase, tyrosinase, peroxidase, sulfhydryl oxidase and protein glutaminase in a known manner. The transglutaminase enzyme (EC 2.3.2.13) catalyzes the generation of covalent linkages between the glutamine and lysine amino acid residues present in the protein molecules. When linkages are formed, ammonia is released. The enzyme was first used in Japan in the manufacture of surimi (seafish paste) products (Kuraishi, et. al., Food Rev. Int. 17(2), 2001, pp. 221 to 246). Covalent bonds formed in the enzyme treatment withstand different process conditions, such as heating and mixing, well. From milk proteins, caseins and particularly the κ-caseins, are the best substrate for transglutaminase. β-casein is also rich in glutamine and lysine, which are linked together by transglutaminase.

It is known that milk contains substances that inhibit the activity of transglutaminase. These inhibiting substances are deactivated in a heat treatment of milk. On the other hand, it is known that the content of said substances in relation to the total content of proteins and fat is reduced in ultrafiltration of milk.

Meat analogs based on plant proteins, especially soy proteins are commercially available. In recent years methods for preparing meat analogs from milk and egg proteins in addition to plant proteins have been developed and such processes are described in the patent publications EP 1467628 B1, EP 1588626 B1, EP 1643850 B1 and EP 1772060 B1, for example.

BRIEF DESCRIPTION OF THE INVENTION

The present invention relates to a process for producing a casein protein product having microstructure similar type to a meat analogue, comprising the steps of:
a) providing a casein concentrate starting material
b) optionally concentrating the casein concentrate material
c) heat-treating the material
d) cooling the heat-treated material
e) subjecting the cooled material to a treatment with a crosslinking enzyme
f) optionally subjecting the cooled material to a treatment with a coagulant
g) processing the material into the casein protein product/ allowing the casein protein product to form
h) optionally collecting and/or packing the product.

The present invention relates also to a casein protein product comprising milk proteins from about 9 to about 50 weight-%, of which about 8.5 to about 50 weight-% are casein proteins, lactose 0 to about 2%, calcium from about 1300 mg/kg to about 12500 mg/kg, phosphorus about 1600 to about 8000 mg/kg and optionally biologically active peptides (tripeptides IPP and/or VPP) from about 20 to about 700 mg/kg. In one embodiment, the product comprises milk proteins from about 15 to about 30 weight-%, of which about 14.5 to about 30 weight-% are casein proteins. In another embodiment, the casein protein product comprises calcium from about 4000 to about 7000 mg/kg.

The objects of the invention are achieved by methods and products characterized by what is stated in the independent claims. The preferred embodiments of the invention are disclosed in the dependent claims.

DETAILED DESCRIPTION OF THE INVENTION

There is currently a continuous need for meat substituting protein products in the market. The present invention is based on the finding that treating a casein concentrate material with a crosslinking enzyme and optionally with a coagulant produces a casein protein product having microstructure similar to a meat analogue. Accordingly, the invention relates to a process for producing a casein protein product, comprising the steps of:
a) providing a casein concentrate starting material,
b) optionally concentrating the casein concentrate material,
c) heat-treating the material,
d) cooling the heat-treated material,
e) subjecting the cooled material to a treatment with a crosslinking enzyme,
f) optionally subjecting the cooled material to a treatment with a coagulant,
g) processing into a casein protein product/allowing a casein protein product to form,
h) optionally collecting and/or packing the product.

In one embodiment, the casein concentrate material is treated with a crosslinking enzyme and with a coagulant to produce a casein protein product having microstructure similar to a meat analogue. Accordingly, the invention relates to a process for producing a casein protein product, comprising the steps of:

a) providing a casein concentrate starting material,
b) optionally concentrating the casein concentrate material,
c) heat-treating the material,
d) cooling the heat-treated material,
e) subjecting the cooled material to a treatment with a crosslinking enzyme,
f) subjecting the cooled material to a treatment with a coagulant,
g) processing into a casein protein product/allowing a casein protein product to form,
h) optionally collecting and/or packing the product.

Casein concentrate starting material refers to a casein concentrate comprising casein as the main milk protein component, lactose, calcium ions, phosphate ions and only minor amounts of whey protein. In one embodiment, the casein concentrate contains about 9-about 12 weight-% milk proteins of which 0-about 0.5 weight-% are whey proteins. In a certain embodiment, the casein concentrate contains about 8-about 11 weight-% caseins. In a certain embodiment, the casein concentrate contains about 9.15 weight-% milk proteins of which about 8.5 weight-% are caseins and about 0.2 weight-% are whey proteins.

In one embodiment, the casein concentrate can be obtained from a milk raw material by a membrane filtration procedure comprising microfiltration, ultrafiltration, nanofiltration, reverse osmosis and/or evaporation.

Accordingly, the present invention relates to a process for producing a casein protein product, comprising the steps of:
a) providing a milk raw material,
b) subjecting the milk raw material to membrane filtration procedure to produce a casein concentrate,
c) optionally concentrating the casein concentrate,
d) heat-treating the casein concentrate,
e) cooling the heat-treated material,
f) optionally subjecting the cooled material to a treatment with a crosslinking enzyme,
g) subjecting the cooled material to a treatment with a coagulant,
h) processing the material into the casein protein product,
i) optionally collecting and/or packing the product.

In another embodiment, the casein concentrate starting material can be obtained from a caseinate.

Accordingly, the present invention relates to a process for producing a casein protein product, comprising the steps of:
a) providing casein concentrate based on a caseinate,
b) optionally concentrating the casein concentrate,
c) heat-treating the casein concentrate,
d) cooling the heat-treated material,
e) subjecting the cooled material to a treatment with a crosslinking enzyme,
f) optionally subjecting the cooled material to a treatment with a coagulant,
g) processing the material into the casein protein product,
h) optionally isolating and/or packing the product.

In the heat-treatment step, the casein concentrate is heated up to a temperature of at least 80° C. In one embodiment, the casein concentrate is heated up to a temperature from 80° C. to 155° C. In another embodiment, the casein concentrate is heated up to a temperature of 80° C. Further, in one embodiment, the casein concentrate is kept in a temperature of at least 80° C. for 5 to 30 minutes.

In the cooling step, the casein concentrate is allowed to cool or is cooled to a temperature below 40° C. In one embodiment, the casein concentrate is allowed to cool or is cooled to a temperature from 2° C. to 20° C. In another embodiment, the casein concentrate is allowed to cool or is cooled to a temperature from 2° C. to 10° C.

In the step of treating with a crosslinking enzyme, the casein concentrate is modified with a crosslinking enzyme. The crosslinking enzyme suitable for use in the process of the invention may be any enzyme that is known to crosslink milk proteins. These enzymes include transglutaminase, laccase, tyrosinase, peroxidase, sulfhydryl oxidase, glucose oxidase and protein glutaminase, for example. Said enzymes can be used alone or in any combinations with each other. The enzyme is typically used in an amount of 0.2 U enzyme/g protein to about 20 U enzyme/g protein, preferably about 3 U enzyme/g protein.

In an embodiment of the invention, the crosslinking enzyme is transglutaminase (EC 2.3.2.13). It is commonly known that transglutaminase catalyzes the generation of covalent linkages between the glutamine and lysine amino acid residues present in the protein molecules. Of milk proteins, caseins, in particular K-casein, are the best substrates for a transglutaminase. β-casein, too, is rich in glutamine and lysine that the enzyme links together. Transglutaminase can be any transglutaminase commonly used in dairy industry. It can be derived from a microbial source, fungus, mould, fish and a mammal. In an embodiment of the invention, transglutaminase is isolated from a microbial source. There are several commercially available transglutaminase enzyme preparations that are suitable for use in the process of the invention. These include Activa®YG (Ajinomoto, Japan), Activa®MP (Ajinomoto, Japan), and Yiming-TG (Yiming Fine Chemicals Co., Ltd., China). Optimum conditions depend on the enzyme used and they can be obtained from the manufacturers of the commercial enzymes.

In another embodiment, the crosslinking enzyme is selected from laccase, tyrosinase, peroxidase, sulfhydryl oxidase, glucose oxidase and/or protein glutaminase. Laccases (EC 1.10.3.2) derived from fungi and bacteria, such as, fungus *Trametes hirsute*, catalyze the crosslinking between carbohydrates and proteins (oxidation of aromatic compounds and cysteine) with applications in food processing for reduction of allergenicity, for example. Tyrosinases (EC 1.14.18.1) are enzymes which catalyzes the oxidation of phenols such as tyrosine, with applications in food processing for reduction of allergenicity, for example. Tyrosinases can be derived from a variety of plant, animal and fungal species, i.e. filamentous fungus *Trichoderma reesei*. Peroxidases (EC 1.11.1.7) are a family of enzymes that catalyze the oxidation of aromatic compounds with applications in food processing for reduction of allergenicity, for example. Sulfhydryl oxidase (EC 1.8.3.3) catalyzes the formation of disulfide bonds, oxidation of glutathione. Glucose oxidase catalyzes the formation of protein crosslinks and oxidate gelation of pentosans. Protein glutaminase (PG) catalyzes the deamidation of protein bound glutamine, and glutamine is converted to glutamic acid.

In the step of treating with a coagulant, the casein concentrate is modified with an agent generating coagulation or simultaneous clotting and gel forming in the material. Suitable agents are acidifiers or ferment like starters, acids and acidogens, such as glucono delta-lactone (GDL), lactic acid, citric acid, hydrochloric acid, oxalic acid, and coagulants, like rennet and chymosin, and calcium salts. In one embodiment, the agent is rennet or chymosin. Chymosin is the active enzyme in rennet. Chymosin cleavages the peptide bond between 105 and 106, phenylalanine and methionine, in kappa-casein. Coagulant is used in a sufficient amount. The chymosin enzyme is typically used in an amount from about 0.0001% to about 0.05%, preferably about 0.002%.

Crosslinking enzyme treatment and coagulation treatment of the casein concentrate can be done simultaneously or sequentially in either order. In one embodiment, crosslinking enzyme treatment and coagulation are done simultaneously. In another embodiment, crosslinking enzyme treatment is done first followed by coagulation. In a further embodiment, coagulation is done first followed by crosslinking enzyme treatment. In a preferred embodiment, cross-linking enzyme treatment and coagulation are done simultaneously. In another preferred embodiment, coagulation is done first followed by crosslinking enzyme treatment. In addition, in one embodiment the temperature during the treatment with a crosslinking enzyme and coagulation is in the range of about 2° C. to about 20° C. In another embodiment the temperature during crosslinking enzyme treatment and coagulation is in the range of about 2° C. to about 10° C. It is important that the whey does not separate during the crosslinking enzyme and coagulation treatment(s).

In the present invention, the casein concentrate material can be produced by membrane filtration of a milk raw material.

For fractionation of casein from milk raw material, filtration techniques, such as microfiltration, ultrafiltration, nanofiltration, reverse osmosis or their combinations, can be used.

The membrane filtrations, such as ultrafiltration and microfiltration, can be performed with diafiltration technique.

Microfiltration of the milk raw material is performed in such a manner that the milk raw material is concentrated by a factor of 1 to 4.5 times by volume, preferably 3.5 to 4.5 times by volume. The concentration factor (cf=K) refers to the ratio of the volume of the liquid fed to the filtration to the retentate, and it is defined with the following formula: K=feed (L)/retentate (L) (L=volume). The concentration factor of ultrafiltration is typically in the range of 1 to 10. In an embodiment, the concentration coefficient is 2 to 5. In one embodiment, the microfiltration is performed in a temperature below 20° C. In another embodiment the microfiltration is performed in a temperature range of 2° C. to 20° C. In a further embodiment the temperature during microfiltration is in the range of 10° C. to 14° C.

The microfiltration of the milk raw material retains major portion of the casein in the retentate whereas a major portion of the whey proteins passes into the permeate. The microfiltration is preferably carried out utilizing a uniform transmembrane pressure loop recirculating the retentate through membrane and permeate through permeate site of membrane.

The microfiltration may comprise a plurality of microfiltration steps. Different steps may comprise, for instance, changing of process conditions and/or filtration membranes. A variable condition may be, for instance, filtration temperature, filtration pressure, addition of diafiltration medium (diawater), and/or concentration factor of filtration. Conditions can be changed by one or more variables. In the microfiltration comprising a plurality of microfiltration steps, more than one MF permeate and retentate fractions may be formed.

In one embodiment, the casein concentrate is obtained using a combination of microfiltration, ultrafiltration, nanofiltration and reverse osmosis.

In an embodiment, raw material milk is subjected to a membrane filtration in order to provide a casein concentrate for further treatment with a protein crosslinking enzyme and a coagulant. In the membrane filtration, substances inhibiting the activity of a protein crosslinking enzyme are passed into a permeate while casein protein is concentrated in the retentate. The membrane filtration is preferably carried out, since the substances inhibiting a protein crosslinking enzyme are removed and the enzyme can act actively. Thus, a larger proportion of the milk proteins can be treated with the same transglutaminase amount resulting in increased yields of the casein protein product.

In the context of the present invention, the milk raw material refers to whole milk, cream, low-fat or skim milk, low-lactose or lactose-free milk, or milk reconstituted from milk powder, organic milk or a combination of these. Preferably, the milk raw material is skim milk. The milk raw material may be supplemented by ingredients generally used in producing milk products, such as fat or sugar fractions.

The membrane filtration of the milk raw material provides a casein concentrate starting material containing casein, lactose, and calcium- and phosphate-ions. In one embodiment, the membrane filtration of the milk raw material provides a casein concentrate containing milk proteins about 9-about 50 weight-%, of which about 8.5-about 50 weight-% are caseins, lactose 0-about 2 weight-%, calcium about 2500-about 12500 mg/kg, phosphorus about 1600-about 8000 mg/kg. In one embodiment, the milk protein content is in the range of about 15-about 30 weight-%, of which about 14.5-about 50 weight % are caseins. In another embodiment, the calcium content is in the range of about 4000-about 7000 mg/kg, preferably in the range of about 3000-about 5000 mg/kg. In a further embodiment, the calcium content is about 3200 mg/kg. In an even further embodiment, the casein concentrate contains about 9.15 weight-% milk proteins of which about 8.5 weight-% are caseins and about 0.2 weight-% are whey proteins. In a certain embodiment of the present invention, the membrane filtration of the milk raw material provides a casein concentrate containing milk proteins 9-50 weight-%, of which 8.5-50 weight-% are caseins, lactose 0-0.2 weight-%, calcium 2500-12500 mg/kg, phosphorus 1600-8000 mg/kg. In a certain embodiment, the milk protein content is in the range of 15-30 weight-%, of which 14.5-50 weight-% are caseins. In a certain embodiment, the calcium content is in the range of 4000-7000 mg/kg, preferably in the range of 3000-5000 mg/kg. In a certain embodiment, the calcium content is 3200 mg/kg. In a certain embodiment, the casein concentrate contains 9.15 weight-% milk proteins of which 8.5 weight-% are caseins and 0.2 weight-% are whey proteins.

In the present invention, the casein concentrate material can be derived and/or produced from micellar casein, acid casein, hydrolyzed casein or rennet casein, for example. Micellar casein is ultrafiltered casein extracted from milk without acidification. Acid casein is a dry free flowing high quality protein food ingredient that has been isolated from skim milk. Hydrolysed casein is a soluble, enzymatic digest of casein. Rennet casein is produced by the controlled precipitation of casein from pure, pasteurized skim milk through the action of rennet.

In the present invention, the casein concentrate starting material can be obtained from caseinate. Caseinates, such as sodium caseinate, calcium caseinate and potassium caseinate, are soluble salts of casein. Caseinates provide outstanding nutritional properties, contain all of the essential amino acids, have a protein efficiency ratio (P.E.R.) of 2.5, and have a minimum protein content of 90% (dry solids basis). In one embodiment, the casein material/casein concentrate can be obtained from calcium caseinate.

In the present invention, casein concentrate material can be can be supplemented with milk minerals. A milk mineral refers to, for example, a salt described in publication EP 1061811 B1, i.e. a milk mineral powder known as trademark Valio Milk Mineral Powder VMMP (Valio Oy). Other feasible milk-based mineral products include such trademarks as Capolac® MM-0525 BG (Arla Foods Ingredients), Vitalarmor CA (Armor Proteins) and Sodidiet 40 MI (Sodiaal Industrie).

The casein concentrate of the present invention comprises casein as the main milk protein component, lactose, and calcium- and phosphate-ions. The casein concentrate of the present invention may contain minor amounts of whey protein(s). Typically, the casein concentrate comprises whey proteins up to about 0.5 weight-%, at the maximum. If the casein concentrate of the present invention contains whey proteins in higher amounts, or in or up to the amount typical to cow's milk i.e., up to or in the casein:whey ratio of about 80:20, the structure of the casein protein product produced from such concentrate would not be strong for a meat substitute, for example. In one embodiment, the casein concentrate comprises milk proteins about 9-about 50 weight-% of which 0-about 0.5 weight-% are whey proteins and about 8.5-about 50 weight-% are caseins, lactose 0-about 2 weight-%, calcium about 2500 mg/kg-about 12500 mg/kg and phosphorus about 1600-about 8000 mg/kg. In one embodiment, the milk protein content is in the range of about 15-about 30 weight-% of which 0-about 0.5% are whey proteins and about 14.5-about 50 weight-% are caseins. In another embodiment, the calcium content is in the range of about 4000-about 7000 mg/kg, preferably in the range of about 3000-about 5000 mg/kg. In a further embodiment, the calcium content is about 3200 mg/kg. In another embodiment, the casein concentrate is concentrated by evaporation to contain from about 9 to about 50 weight-% casein. In another embodiment casein powder is reconstituted to solution having casein content of about 9-about 50 weight-%. In an even further embodiment, the casein concentrate contains about 9.15 weight-% milk proteins of which about 8.5 weight-% are caseins and about 0.2 weight-% are whey proteins. In a certain embodiment, the casein concentrate comprises milk proteins 9-50 weight % of which 0-0.5 weight % are whey proteins and 8.5-50 weight-% are caseins, lactose 0-2 weight-%, calcium 2500 mg/kg-12500 mg/kg and phosphorus 1600-8000 mg/kg. In one embodiment, the milk protein content is in the range of 15-30 weight-% of which 0-0.5% are whey proteins and 14.5-50 weight-% are caseins. In another embodiment, the calcium content is in the range of 4000-7000 mg/kg, preferably in the range of 3000-5000 mg/kg. In a further embodiment, the calcium content is 3200 mg/kg. In another embodiment, the casein concentrate is concentrated by evaporation to contain 9-50 weight-% casein. In another embodiment, casein powder is reconstituted to solution having casein content of 9-50 weight-%. In a certain embodiment, the casein concentrate contains 9.15 weight-% milk proteins of which 8.5 weight-% are caseins and 0.2 weight-% are whey proteins. In a certain embodiment, the casein concentrate contains caseins about 8.5-about weight-11%, whey proteins about 0.2-about 0.5 weight-%, lactose about 0.4-about 1.0 weight-%, calcium about 2500 to about 4000 mg/kg, phosphorus about 1600 to about 2000 mg/kg, magnesium about 130 to about 150 mg/kg, sodium about 86 to about 100 mg/kg and potassium about 340 to about 500 mg/kg.

In one embodiment, the present invention relates to a process for producing a casein protein product, comprising the steps of:
   a) providing casein concentrate comprising milk proteins about 9-about 50 weight-%, of which about 8.5-about 50 weight-% are caseins,
   b) optionally concentrating the casein concentrate,
   c) heat-treating the casein concentrate to a temperature from 80° C. to 155° C.,
   d) cooling the heat-treated material to a temperature from 2° C. to 20° C.,
   e) subjecting the cooled material to a treatment with a transglutaminase enzyme,
   f) optionally subjecting the cooled material to a treatment with a rennet and/or chymosin,
   g) processing the material into the casein protein product,
   h) optionally isolating and/or packing the product.

In another embodiment, the present invention relates to a process for producing a casein protein product, comprising the steps of:
   a) providing casein concentrate comprising milk proteins about 9-about 50 weight-%, of which about 8.5-about 50 weight-% are caseins, lactose 0-about 2 weight-%, calcium about 2500-about 12500 mg/kg and phosphorus about 1600-about 8000 mg/kg,
   b) optionally concentrating the casein concentrate,
   c) heat-treating the casein concentrate to a temperature from 80° C. to 155° C.,
   d) cooling the heat-treated material to a temperature from 2° C. to 20° C.,
   e) subjecting the cooled material to a treatment with a transglutaminase enzyme,
   f) optionally subjecting the cooled material to a treatment with a rennet and/or chymosin,
   g) processing the material into the casein protein product,
   h) optionally isolating and/or packing the product.

In a further embodiment, the present invention relates to a process for producing a casein protein product, comprising the steps of:
   a) providing casein concentrate comprising milk protein milk proteins about 15-about 30 weight-%, of which about 14.5-about 30 weight-% are caseins,
   b) optionally concentrating the casein concentrate,
   c) heat-treating the casein concentrate to a temperature from 80° C. to 155° C.,
   d) cooling the heat-treated material to a temperature from 2° C. to 20° C.,
   e) subjecting the cooled material to a treatment with a transglutaminase enzyme,
   f) optionally subjecting the cooled material to a treatment with a rennet and/or chymosin,
   g) processing the material into the casein protein product,
   h) optionally isolating and/or packing the product.

The process of the invention may further contain additional optional process steps, such as homogenisation and/or a further-processing step in which the casein concentrate based material is treated in a manner required by the product being prepared, for instance by adding ingredients, mixing and/or recovering the product in a manner characteristic to it. These optional steps are performed in an appropriate stage of the process known by a person skilled in the art. The selection of suitable optional steps and conditions belongs to knowledge of a person skilled in the art.

The invention relates also to a casein protein product produced with the method described herein.

In addition, the present invention relates also to a casein protein product comprising milk proteins about 9-about 50 weight-%, of which about 8.5-about 50 weight-% are caseins and 0-about 0.5 weight-% are whey proteins. In one embodiment, the casein protein product further comprises lactose from 0-about 2 weight-%, calcium from about 1300 to about 12500 mg/kg, phosphorus from about 1600 to about 8000 mg/kg and optionally biologically active peptides (tripeptides IPP and/or VPP) from about 20 to about 700 mg/kg. In one embodiment, the casein protein product comprises milk proteins about 15-about 30 weight-%, of which about 14.5-about 30 weight-% are caseins. In another embodiment, the calcium content is in the range of about 4000-about 7000 mg/kg, preferably in the range of about 3000-about 5000 mg/kg. In a further embodiment, the calcium content is about 3200 mg/kg. In an even further embodiment, the casein protein product contains about 9.15 weight-% milk proteins of which about 8.5 weight-% are caseins and about 0.2 weight-% are whey proteins. In a certain embodiment, the casein protein product contains milk proteins 9-50 weight-%, of which 8.5-50 weight-% are caseins. In a certain embodiment, the casein protein product further comprises, lactose 0-0.2 weight-%, calcium 2500-12500 mg/kg, phosphorus 1600-8000 mg/kg. In a certain embodiment, the milk protein content of the casein protein product is in the range of 15-30 weight-%, of which 14.5-30 weight-% are caseins. In a certain embodiment, the calcium content is in the range of 4000-7000 mg/kg, preferably in the range of 3000-5000 mg/kg. In a certain embodiment, the calcium content is 3200 mg/kg. In a certain embodiment, the casein protein product contains 9.15 weight-% milk proteins of which 8.5 weight-% are caseins and 0.2 weight-% are whey proteins. In a certain embodiment, the casein protein product comprises milk proteins about 9-about 50 weight-%, of which about 8.5-about 50 weight-% are caseins and 0-about 0.5 weight-% are whey proteins, lactose from 0-about 2 weight-%, calcium from about 1300 to about 12500 mg/kg, phosphorus from about 1600 to about 8000 mg/kg and biologically active peptides (tripeptides IPP and/or VPP) from about 20 to about 700 mg/kg.

If the casein protein product of the present invention contains whey proteins in higher amounts, or up to or in the amount typical to cow's milk i.e., up to or in the casein:whey ratio of about 80:20, the product would not have a microstructure similar to a meat analogue and accordingly the texture of the product would not be strong enough for a meat substitute. In addition, lactose, which is typically included in the whey protein fraction, makes the product sweet and further when whey proteins are heated, the flavor of cooked milk is formed in the product. Accordingly, it is critical for the casein protein product of the present invention, that the amount of whey proteins in the product is low (about 0.5. weight-% at the maximum).

Additionally, the casein protein product may comprise fats and/or oils, such as palm oil, rape and rapeseed oil, linseed oil, olive oil, corn oil, sunflower oil, cream, butter oil or combinations or mixtures thereof. The milk protein product of the present invention has pH in the range of 5.5 to 6.7.

The casein protein product may also comprise hydrocolloids and/or polysaccharides such as alginates, pectins, carrageenan, locust bean gum, guar gum, gellan gum, xanthan gum, acacia gum, carob, beta-glucan, arabinoxylan, carboxymethyl cellulose (CMC), polydextrose, bacterial exopolysaccharides and starches derived from potato, maize, pea, rice, wheat, tapioca and durra, for example.

The casein protein product of the present invention can be seasoned/flavoured by adding desired spices and/or herbs to the casein material during the manufacturing process or by adding the desired spices and/or herbs to the inner surface of the moulding tube or to the casein protein base during the processing of the material into the casein protein product.

The casein protein product of the present invention can be used as a meat substitute/meat analogue eaten as such, heated, cooked, fried or grilled like meat.

The following examples are presented to further illustration of the invention without limiting the invention thereto.

Example 1

A casein concentrate (2000 L) obtained from microfiltration and having a casein content of at least 9 weight-% was heated up to a temperature above 80° C. The casein solution was allowed to cool to a temperature of 40° C. and it was dispensed in moulds. Transglutaminase (1 U/g protein) and chymosin enzymes (0.0001%) were added to the solution and the casein protein product was allowed to form by coagulation in the room temperature.

Casein protein product: protein 10 weight-%, lactose 0.9 weight-%, calcium 2500 mg/kg, phosphorus 1600 mg/kg and biologically active peptides 300 mg/kg.

Example 2

A filtered casein solution (2000 L) was concentrated at 90° C. by evaporating.

The concentrated solution (1000 L) was cooled to a temperature below 10° C. and transglutaminase and chymosin enzymes were added. The solution was dispensed into so-called moulding tube having a flavoring mixture integrated into its inner surface. The casein solution was allowed to coagulate in the tube in the room temperature. The milk protein product in tube was cooled to a temperature of +2° C. to +4° C. The formed casein protein product was cut into pieces or slices of desired thickness which were packed with an inert gas.

Casein protein product: protein 19 weight-%, lactose 0.3 weight-%, calcium 5000 mg/kg, phosphorus 3200 mg/kg and biologically active peptides 400 mg/kg.

Example 3

Skim milk was microfiltered to a casein solution (2000 L) which was further concentrated by ultrafiltration (concentration factor 2-3) to casein concentrate (15-20 weight-% protein). The concentrated solution (700-1000 L) was heated up to a temperature of 80° C.-150° C. Then the solution was cooled to a temperature below 10° C. and chymosin and transglutaminase were added thereto and the casein protein product was allowed to form by coagulation in the room temperature.

Casein protein product: protein 19-30 weight-%, lactose 0.8-1.2 weight-%, calcium 5000-8000 mg/kg, phosphorus 3000-4200 mg/kg and biologically active peptides 500-650 mg/kg.

Example 4

Casein in powder form was reconstituted in water or in a concentrated filtration solution described in Example 1 or in Example 2 to give a solution having protein content of 20-50 weight-%.

The solution was heated up to a temperature of 80° C.-150° C. Then the solution was cooled to a temperature below 10° C. and chymosin and transglutaminase were added thereto. The solution was dispensed into so-called moulding tube having a flavoring mixture integrated into its inner surface and allowed to coagulate in the tube in the room temperature. The casein protein product in tube was cooled to a temperature of +2° C. to +4° C. The formed milk protein product was cut into pieces or slices of desired thickness which were packed with an inert gas.

Casein protein product: protein 50 weight-%, lactose 1.5 weight-%, calcium 12300 mg/kg, phosphorus 5000 mg/kg and biologically active peptides 650 mg/kg.

Example 5

A filtered casein solution was heated up to a temperature above 80° C. The solution was cooled to a temperature of 40° C. and then chymosin was added to the casein solution. The solution was dried into a powder which was reconstituted in water to give a solution having protein content of 20-50% and heated up to a temperature above 80° C. The solution was cooled to a temperature below 10° C. and transglutaminase was added thereto. The solution was dispensed into a so-called moulding tube having a flavoring mixture integrated into its inner surface. The casein solution was allowed to coagulate in the tube in the room temperature. The milk protein production tube was cooled to a temperature of +2° C. to +4° C. The formed casein protein product was cut into pieces or slices of desired thickness which were packed with an inert gas.

Casein protein product: protein 47 weight-%, lactose 1 weight-%, calcium 10000 mg/kg, phosphorus 3500 mg/kg and biologically active peptides 500 mg/kg.

Example 6

Casein concentrate was produced as follows: raw milk was skimmed and pasteurized at 73° C. for 15 s. The resultant pasteurized skim milk was subjected to microfiltration (MF) and recirculated through membranes of a pore size 0.08 μm at a temperature of 13° C. to concentrate casein in a MF retentate. Water, a major portion of whey protein and part of the lactose and milk minerals passed through the membrane to a permeate. Casein retentate (i.e. casein concentrate) having the total solids of about 9 weight-% to 12 weight-% was optionally further processed to higher dry weight by evaporation or spray drying (or freeze drying) to the total solids of 20 weight-% up to 95 weight-%.

The composition of the casein retentate/casein concentrate (total solids of about 9 to about 12 weight-%) is:

Casein about 8.5 to 11 weight-%
Whey protein about 0.2 to 0.5 weight-%
Lactose about 0.4 to 1.0 weight-%
Calcium about 2500 to 4000 mg/kg
Phosphorus about 1600 to 2000 mg/kg
Magnesium about 130 to 150 mg/kg
Sodium about 86 to 100 mg/kg
Potassium about 340 to 500 mg/kg It will be obvious to a person skilled in the art that, as the technology advances, the inventive concept can be implemented in various ways. The invention and its embodiments are not limited to the examples described above but may vary within the scope of the claims.

The invention claimed is:

1. A process for producing a casein protein product, comprising the steps of:
    a) providing a casein concentrate starting material, wherein the casein concentrate starting material comprises milk proteins 9-50 weight-%, and wherein 8.5-50 weight-% of the casein concentrate starting material are caseins,
    b) optionally concentrating the casein concentrate material,
    c) heat-treating the material up to a temperature from 80° C. to 155° C.,
    d) cooling the heat-treated material,
    e) subjecting the cooled material to a treatment with a crosslinking enzyme,
    f) optionally subjecting the cooled material to a treatment with a coagulant,
    g) processing the material into the casein protein product having a pH in the range of 5.5 to 6.7, and
    h) optionally isolating and/or packing the product,
    wherein the casein protein product is a meat substitute.

2. The process according to claim 1, wherein the process comprises the additional steps of:
    a) providing a milk raw material, and
    b) subjecting the milk raw material to membrane filtration procedure for producing the casein concentrate.

3. The process according to claim 1, wherein the cooled material is subjected to a treatment with a coagulant.

4. The process according to claim 1, wherein the casein concentrate comprises milk proteins 15-30 weight-%, and wherein 14.5-30 weight-% of the casein concentrate are caseins.

5. The process according to claim 1, wherein the casein concentrate further comprises lactose in an amount of 0-2 weight-%, calcium in an amount of 2500-12500 mg/kg and phosphorus in an amount of 1600-8000 mg/kg.

6. The process according to claim 1, wherein the casein concentrate further comprises calcium in an amount of 4000-7000 mg/kg.

7. The process according to claim 1, wherein the casein concentrate further comprises phosphorous in an amount of 3000-5000 mg/kg.

8. The process according to claim 1, wherein in the cooling step (d) the material is cooled to a temperature from 2° C. to 20° C.

9. The process according to claim 1, wherein the crosslinking enzyme is a transglutaminase.

10. The process according to claim 1, wherein the coagulant is rennet or chymosin.

11. The process according to claim 1, wherein the process comprises at least one additional step selected from the group consisting of steps:
    a) concentrating the casein concentrate material,
    b) subjecting the cooled material to a treatment with a coagulant, and
    c) isolating and/or packing the product.

* * * * *